US00PP18585P2

(12) United States Plant Patent
Faria

(10) Patent No.: US PP18,585 P2
(45) Date of Patent: Mar. 11, 2008

(54) ***EUPHORBIA* PLANT NAMED 'BONFIRE'**

(50) Latin Name: *Euphorbia epithymoides*
Varietal Denomination: Bonfire

(75) Inventor: Mary Ann Faria, Lincoln, RI (US)

(73) Assignee: Limerock Plant Farm, Lincoln, RI (US)

( * ) Notice: Subject to any disclaimer, the term of this patent is extended or adjusted under 35 U.S.C. 154(b) by 214 days.

(21) Appl. No.: 11/324,477

(22) Filed: Dec. 31, 2005

(51) Int. Cl.
*A01H 5/00* (2006.01)

(52) U.S. Cl. ..... Plt./302

(58) Field of Classification Search ..... Plt./302
See application file for complete search history.

*Primary Examiner*—Anne Marie Grunberg
*Assistant Examiner*—Georgia Helmer
(74) *Attorney, Agent, or Firm*—C. A. Whealy

(57) ABSTRACT

Anew and distinct cultivar of *Euphorbia* plant named 'Bonfire', characterized by its compact and mounding plant habit; freely branching growth habit; dark red purple-colored foliage; yellow to red-colored foral bracts; and tightly clustered cyathia.

1 Drawing Sheet

Botanical designation: *Euphorbia epithymoides.*
Cultivar denomination: 'Bonfire'.

BACKGROUND OF THE INVENTION

The present invention relates to a new and distinct cultivar of *Euphorbia,* botanically known as *Euphorbia epithymoides* and hereinafter referred to by the cultivar name Bonfire.

The new *Euphorbia* is a product of a planned breeding program conducted by the Inventor in Lincoln, Rhode Island. The objective of the breeding program is to create new *Euphorbia* cultivars with red-colored leaves.

The new *Euphorbia* originated from an open pollination in May, 1999 in Lincoln, Rhode Island, of a unnamed seedling selection of *Euphorbia epithymoides,* not patented, as the female, or seed, parent with an unknown selection of *Euphorbia epithymoides,* as the male, or pollen, parent. The cultivar Bonfire was discovered and selected by the Inventor as a flowering plant within the progeny of the stated open pollination during the spring of 2000 in a controlled environment in Lincoln, Rhode Island.

Asexual reproduction of the new *Euphorbia* by terminal cuttings in a controlled environment in Lincoln, Rhode Island, has shown that the unique features of this new *Euphorbia* are stable and reproduced true to type in successive generations.

SUMMARY OF THE INVENTION

The cultivar Bonfire has not been observed under all possible environmental conditions. The phenotype may vary somewhat with variations in environment such as temperature and light intensity without, however, any variance in genotype.

The following traits have been repeatedly observed and are determined to be the unique characteristics of 'Bonfire'. These characteristics in combination distinguish 'Bonfire' as a new and distinct *Euphorbia* cultivar:

1. Compact and mounding plant habit.
2. Freely branching growth habit.
3. Dark red purple-colored foliage.

4. Yellow to red-colored floral bracts.
5. Tightly clustered cyathia.

Plants of the new *Euphorbia* differ primarily from plants of the female parent selection in leaf coloration as plants of the female parent selection have green-colored leaves. In addition, plants of the new *Euphorbia* are more compact and more uniform than plants of the female parent selection.

Plants of the new *Euphorbia* can be compared to plants of the *Euphorbia epithymoides* cultivar First Blush, disclosed in U.S. Plant Pat. No. 15,292. Plants of the new *Euphorbia* and the cultivar First Blush differ primarily in leaf coloration as plants of the cultivar First Blush have white, green and pink-colored leaves. In addition, plants of the new *Euphorbia* are more compact and more mounding than plants of the cultivar First Blush.

BRIEF DESCRIPTION OF THE PHOTOGRAPH

The accompanying colored photograph illustrates the overall appearance of the new *Euphorbia,* showing the colors as true as it is reasonably possible to obtain in colored reproductions of this type. Colors in the photograph may differ slightly from the color values cited in the detailed botanical description which accurately describe the colors of the new *Euphorbia.* The photograph comprises a side perspective view of a typical plant of 'Bonfire' grown in an outdoor nursery.

DETAILED BOTANICAL DESCRIPTION

The following observations, measurements and values describe plants grown in Northern Texas, during the spring and early summer under outdoor field conditions which closely approximate commercial production. Plants used for the photographs and the description were about one year old. In the description, color references are made to The Royal Horticultural Society Colour Chart, 1995 Edition, except where general terms of ordinary dictionary significance are used.

Botanical classification: *Euphorbia epithymoides* cultivar Bonfire.

Parentage:

*Female, or seed, parent.*—Unnamed seedling selection of *Euphorbia epithymoides,* not patented.

*Male, or pollen, parent.*—Unknown selection of *Euphorbia ephithymoides,* not patented.

Propagation:

*Type.*—By terminal cuttings.

*Time to initiate roots, summer.*—About 18 days at temperatures of 37° C.

*Time to initiate roots, winter.*—About 20 days at temperatures of 17° C.

*Time to produce a rooted young plant, summer.*—About 30 days at temperatures of 37° C.

*Time to produce a rooted young plant, winter.*—About 40 days at temperatures of 17° C.

*Root description.*—Fine; white in color.

Plant description:

*Plant form and growth habit.*—Compact and mounding plant habit; perennial subshrub.

*Branching habit.*—Freely branching, usually about 30 lateral branches per plant.

*Plant height, soil level to top of flowers.*—About 30 cm.

*Plant diameter, area of spread.*—About 32 cm.

*Lateral branch description.*—Length: About 28 cm. Diameter: About 5 mm. Internode length: About 1.4 cm. Strength: Strong, flexible. Texture: Smooth. Color: 144A to 144B overlain with close to 59A to 187A.

Foliage description:

*Stem leaves.*—Arrangement: Alternate, single; sessile. Length: About 11 cm. Width: About 3 cm. Shape: Elongated oblong. Apex: Acute. Base: Mostly attenuate. Margin Entire. Texture: Glabrous, smooth. Color: Developing foliage, upper and lower surfaces; Initially close to 46C then becoming closer to 144A overlain with close to 59A to 187A. Fully developed foliage, upper surface: More green than 146A to close to 147A overlain with close to 59A to 187A; venation, similar to lamina. Fully developed foliage, lower surface: Close to 147B; venation, similar to lamina.

*Whorl leaves.*—Quantity/arrangement: One to three whorls of about five each at the base of inflorescences. Length: About 5.25 cm. Width: About 2 cm. Shape: Narrowly ovate to elongated oblong. Apex: Acute. Base: Attenuate to slightly cordate. Margin: Entire. Texture: Glabrous, smooth. Color: Developing and fully expanded foliage, upper surface: Close to 144A to 146A; central area, close to 59A; venation, similar to lamina. Developing and fully expanded foliage, lower surface: Close to 146A; venation, similar to lamina.

Flower description:

*Natural flowering season.*—Late spring to early summer in the Northern Hemisphere.

*Flower arrangement.*—Flowers arranged in umbel-like compound cymes. Very freely flowering with numerous flowers per plant. Flowers mostly upright; persistent; and not fragrant.

*Inflorescence diameter.*—About 7.5 cm.

*Inflorescence height.*—About 2.5 cm.

*Flower diameter.*—About 1.8 cm.

*Flower height.*—About 7.5 mm.

*Flower longevity.*—About three to four weeks on the plant.

*Floral bracts.*—Quantity/arrangement: Usually two or three, opposite or in a whorl subtending the cyathium. Length: About 7.5 mm. Width: About 7 mm. Shape: Broadly ovate. Apex: Acute. Base: Attenuate. Margin: Entire. Texture: Glabrous; smooth. Color, upper and lower surfaces: 9A overlain with close to 46A to 59A.

*Cyathia.*—Arrangement: Involucre of cyathium cup-shaped; 4-lipped; upright. About three petaloid appendages subtending the cyathia, 2 mm by 1 mm, bright yellow, close to 9A, color becoming closer to 46A to 46B with development. Height: About 3 mm. Diameter: About 4.5 mm. Color: Close to 9A.

*Pedicels.*—Length: About 1 cm. Diameter: About 1 mm. Angle: Erect to about 20° from vertical. Strength: Strong, flexible. Texture: Smooth. Color: Close to 144A.

*Reproductive organs.*—Androecium: Stamen number: About two to four. Anther shape: Bi-lobed. Anther length: Less than 1 mm. Anther color: Close to 21A. Amount of pollen: None observed. Gynoecium: Pistil number: One. Pistil shape: Tri-parted. Pistil length: About 3 mm. Style length: About 2 mm. Style color: Close to 154A to 154B. Stigma shape: Bi-lobed. Stigma color: Close to 59A. Ovary color: Close to 144A.

*Seed/fruit.*—Seed and fruit production have not been observed.

Disease/pest resistance: Plants of the new *Euphorbia* have not been observed to be resistant to pathogens or pests common to *Euphorbia.*

Temperature tolerance: Plants of the new *Euphorbia* are tolerant to temperatures from about 0° C. to about 39° C.

It is claimed:

1. A new and distinct *Euphorbia* plant named 'Bonfire', as illustrated and described.

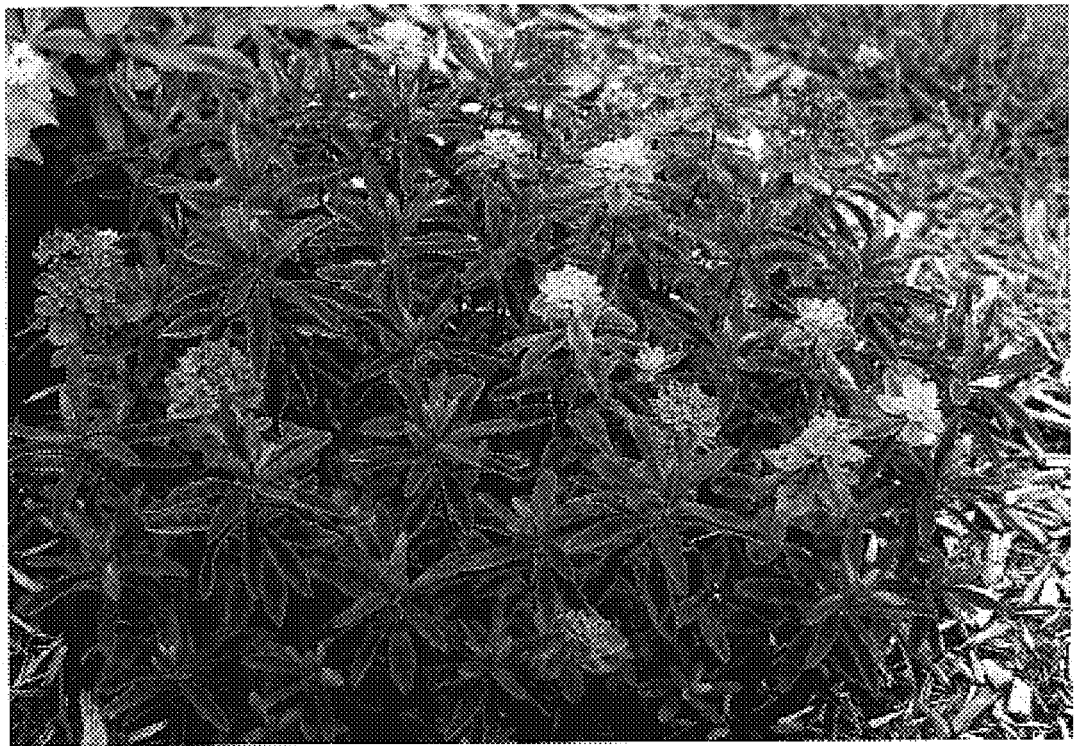

* * * * *